United States Patent [19]
Schuh

[11] Patent Number: 6,126,311
[45] Date of Patent: Oct. 3, 2000

[54] DEW POINT SENSOR USING MEMS

[75] Inventor: William C. Schuh, Delavan, Wis.

[73] Assignee: Claud S. Gordon Company, Richmond, Ill.

[21] Appl. No.: 09/184,359

[22] Filed: Nov. 2, 1998

[51] Int. Cl.$^7$ .......................... G01N 25/02; G01N 11/26
[52] U.S. Cl. ............................ 374/21; 374/16; 374/118; 374/28
[58] Field of Search ................. 374/21, 28, 16, 374/118; 73/31.1, 579

[56] References Cited

U.S. PATENT DOCUMENTS

| | | | |
|---|---|---|---|
| 4,526,011 | 7/1985 | Logan et al. | 374/28 |
| 4,677,416 | 6/1987 | Nishimoto et al. | 374/28 |
| 4,801,211 | 1/1989 | Yagi et al. | 374/28 |
| 4,877,329 | 10/1989 | Sauerbaum et al. | 374/28 |
| 4,898,476 | 2/1990 | Herrmann et al. | 374/28 |
| 4,948,263 | 8/1990 | Herrmann et al. | 374/28 |
| 4,981,369 | 1/1991 | Kumada et al. | 374/28 |
| 5,000,579 | 3/1991 | Kumada et al. | 374/28 |
| 5,275,055 | 1/1994 | Zook et al. | 73/702 |
| 5,365,784 | 11/1994 | Morrissey | 374/16 |
| 5,475,318 | 12/1995 | Marcus et al. | 324/762 |
| 5,533,393 | 7/1996 | Bonne et al. | 374/28 |
| 5,551,283 | 9/1996 | Manaka et al. | 73/31.01 |
| 5,563,341 | 10/1996 | Fenner et al. | 73/29.01 |
| 5,714,791 | 2/1998 | Chi et al. | 257/467 |
| 5,772,322 | 6/1998 | Burns et al. | 374/118 |
| 5,841,217 | 11/1998 | Kizaki et al. | 310/348 |
| 5,966,066 | 10/1999 | Mehregany et al. | 337/70 |
| 6,031,944 | 2/2000 | Younger | 385/12 |
| 6,041,642 | 3/2000 | Duncan | 73/24.01 |
| 6,050,722 | 4/2000 | Thundat et al. | 374/121 |

FOREIGN PATENT DOCUMENTS

| | | |
|---|---|---|
| 1301477 | 5/1992 | Canada . |
| 4104327 | 8/1992 | Germany . |
| 19637735 | 9/1998 | Germany . |
| 56-126738 | 10/1981 | Japan . |
| 59-141038 | 8/1984 | Japan . |
| 62-156550 | 7/1987 | Japan . |
| 1163238 | 6/1985 | Russian Federation . |
| 0954909 | 4/1964 | United Kingdom ............ 374/21 |

OTHER PUBLICATIONS

*Thermoelectricity Theory, Thermometry, Tool,* "Chapter 4—Elementary Thermoelectric Concepts", Daniel D. Pollock, ASTM Special Technical Publication, pp. 111–132.

*Electronics Letters An International Publication,* "Integrated Thin Film Thermoelectric Cooler", Gao Min, D. M. Rowe and F. Volklein, 22$^{nd}$ Jan. 1998, vol. 34, No. 2., pp. 222–223.

(List continued on next page.)

*Primary Examiner*—G. Bradley Bennett
*Assistant Examiner*—G. Verbitsky
*Attorney, Agent, or Firm*—Renner, Otto, Boisselle & Sklar, LLP

[57] ABSTRACT

A dew point sensor includes a micro-cantilever beam formed on a substrate. A cooling device and a temperature sensor are in thermal contact with the micro-cantilever beam and a control circuit is coupled to the micro-cantilever beam, the cooling device and the temperature sensor. The control circuit controls and monitors a resonance of the micro-cantilever beam, controls a temperature of the cooling device and receives a temperature indication from the temperature sensor. Using the above information, the dew point temperature is determined by identifying the temperature of the micro-cantilever beam when its resonance changes due to a change in mass caused by the formation of dew on the micro-cantilever beam when the dew point is reached. A method of determining the dew point is also disclosed. The method includes exciting a micro-cantilever beam in a vibratory mode and decreasing a temperature of the micro-cantilever beam. When the temperature of the micro-cantilever beam reaches the dew point, dew forms thereon, thus changing its mass which causes a resonance of the micro-cantilever beam to change. The resonance of the beam is then monitored to detect the dew point.

22 Claims, 9 Drawing Sheets

OTHER PUBLICATIONS

"Micromechanical Sensors for Chemical and Physical Measurements", E. A. Wachter and T. Thundat, Rev. Scl. Instrum. 66(6), Jun. 1995, *1995 American Institute of Physics*, pp. 3662–3667.

"Improved dew point measurements based on a SAW sensor", Kevin A. Vetelino, Patrick R. Story, Russell D. Mileham, David W. Galipeau, Sensors and Actuators B 35–36 (1996) 91–98, *1996 Elsevier Science S. A.*, pp. 91–98.

Vetelino, et al.; *Improved Dew Point Measurements Based on a Saw Sensor*, Sensors and Actuators B 35–36 (1996) 91–98.

E. Wachter and T. Thundat; *Micromechanical Sensors for Chemical and Physical Measurements*; Rev. Sci. Instrum. 66(6), Jun. 1995, pp. 3662–3667.

DEW POINT SENSOR USING MEMS

TECHNICAL FIELD OF THE INVENTION

The present invention relates to sensors, and more particularly relates to a dew point sensor using microelectromechanical system (MEMS) device technology.

BACKGROUND OF THE INVENTION

There is a strong need for systems and methods for measuring water vapor concentration in the fields of atmospheric science, agriculture, and industry such as the microelectronics, steel, textiles, paper and food industries. Water vapor concentration is typically measured using either dew point sensors or relative humidity sensors. The relative humidity (RH) and the dew point of a gaseous sample are closely related by well known psychometric algorithms for converting dew point and ambient temperature to relative humidity or converting RH and ambient temperature to dew point. The dew point is defined as the temperature at which the partial pressure of water vapor is equal to the vapor pressure of water.

Commercially available dew point sensors such as chilled mirror hygrometers utilize complicated and cumbersome methods to detect the presence of dew on a chilled surface. The detection scheme consists of directing a light beam using a diode laser onto a mirror which reflects the light beam onto a photo detector. While the mirror is dry the reflective characteristics of the mirror are good and a substantial amount of light is received by the photo detector. With the presence of dew on the mirror, however, the reflective characteristics of the mirror change and the light which reflects off the mirror is diffused, thus reducing the amount of light reaching the photo detector. The mirror is in thermal contact with a chiller and is capable of being cooled to below the dew point so that the dew can form on the mirror surface and the temperature at which the dew forms is by definition the dew point of the ambient environment.

A temperature sensor in thermal contact with the mirror provides the measurement of the mirror temperature at the dew point. Therefore by monitoring the amount of light detected by the photo detector, the temperature at which dew forms on the mirror may be determined. While this method is accurate, it is cumbersome and expensive to implement and maintain; for example, contamination of the mirror surface may lead to inaccurate readings or a malfunction of the sensor.

Other prior art sensors such as that disclosed in "*Improved Dew point Measurements Based on a SAW Sensor*", by Vetelino et al. in *Sensors and Actuators*, B35–36(1996), have proposed improvements to the chilled mirror hygrometer. Such prior art solutions utilize surface acoustic wave (SAW) devices to detect the presence of moisture. A SAW sensor generates surface acoustic waves which are transmitted through a delay path using the reverse piezoelectric effect. When the sensor is cooled, condensation forms on its surface which attenuates the wave and alters its velocity. The dew point may then be determined by monitoring the changes in the wave velocity, frequency or phase. This method offers some advantages over the chilled mirror system; however, SAW devices are extremely sensitive to a multitude of physical effects, parameters and variables such as temperature, pressure, and vibration. Isolation or compensation for these parameters is therefore necessary to achieve satisfactory performance of these devices which results in increased complexity and cost.

Another prior art solution in U.S. Pat. No. 4,877,329 (Sauerbaum et al.) discloses a sensor which is chilled to form condensation thereon. The condensation is detected by a comb-like interdigited sensor which outputs a varying electrical signal in response to variations in the thickness of the formed dew layer. For example, the varying electrical signal may be a function of a change in capacitance of the sensor due to a varying amount of moisture in the dielectric caused by variations in the amount of dew. Along with the sensor structure, Sauerbaum et al. teach a method for measuring the dew point that includes cycling a heating and cooling device to maintain a constant layer of dew at the measured dewpoint and a step for calibrating the sensor to avoid errors by displacement of the zero point due to, for example, contamination. While this device and method improve the cost and complexity of a dew point measurement system over a chilled mirror hygrometer, the device is subject to errors and drift in the interdigited sensor material. These problems are well understood to be inherent in the sorption type humidity sensors and a property of the materials commonly chosen to adsorb the moisture.

A related group of prior art sensors measure the relative humidity of an ambient environment as opposed to the dew point. As discussed above, relative humidity and dew point are easily converted from one to the other with a measurement of the ambient air temperature. As disclosed in "*Micromechanical Sensors for Chemical and Physical Measurements*", by E. A. Wachter et al., in *Rev. Sci. Instrum.* 66(6), June 1995, a relative humidity sensor utilizes a micro-cantilever beam (MCL) with a sorption coating of gelatin for measuring humidity. No chilling of the environment is performed since the dew point is not being measured; instead, the MCL's coating changes mass as more water is absorbed at higher humidity levels. This mass change is detected by the shift in a resonant frequency of the MCL. While incorporating a sorption sensor onto a microelectromechanical device would conceivably give a better sensitivity than a standard sorption type sensor, the prior art unit is still plagued by the common problems of sorption type sensors including hysteresis. For example, if the relative humidity of the environment is 50% with a corresponding MCL mass of X, and the relative humidity increases to 90% with a corresponding MCL mass of Y, a subsequent decrease in the relative humidity back to 50% will not result in the MCL mass decreasing back to X, but rather the mass of the MCL will decrease to X+ΔX, wherein ΔX corresponds to an error due to the hysteresis of the sorption film.

Similar to Wachter et al., U.S. Pat. No. 5,563,341 (Fenner et al.) teaches a vapor pressure sensor which utilizes a coating on a restrained or non-vibrating cantilever beam. Changes in vapor pressure of a selected material within the ambient cause stress in the coating and beam which is measured to provide an indication of the vapor pressure. Again, this prior art method offers sensitivity advantages over standard sorption sensors but still suffers from the limitations of these coatings such as hysteresis.

In addition to the undesirable hysteresis impacts of sorption films, sorption materials are typically polymer films which corrode over time. Furthermore, over the lifetime of the film the moisture within the film evaporates which results in the film "drying out", thus resulting in further film degradation which cause variations in its sorption properties, thus further contributing to measurement errors.

There is therefore a need in the art for a dew point sensor having a reduced cost and complexity and which does not suffer from errors inherent in sorption type sensors.

SUMMARY OF THE INVENTION

The present invention relates to a dew point sensor utilizing the mass change of a structure due to dew formation thereon as it reaches the dew point of the ambient environment without the use of a sorption film. The dew point sensor also includes a cooling device for cooling the structure down to the dew point.

According to one aspect of the present invention, a dew point sensor includes a micro-electromechanical system (MEMS) having control circuitry, preferably integrated, for exciting the MEMS into a vibratory mode and detecting shifts in the resonance of the MEMS device. The dew point sensor further includes a temperature sensor and a cooling device such as a thermoelectric chiller in thermal contact with the MEMS device for cycling the temperature of the MEMS device and identifying a temperature at which a change in the resonance of the MEMS device is detected.

The dew point sensor operates by exciting the MEMS device into a vibratory mode, wherein the control circuitry detects the resonant frequency of the MEMS device. The thermoelectric chiller then cools the MEMS device; at a particular temperature the dew point is reached and dew forms on the MEMS device, thereby changing the mass and therefore the resonant frequency of the MEMS device. The control circuitry detects the change in resonant frequency and identifies the temperature via the temperature sensor at which the resonant frequency changed, thus detecting the dew point.

According to another aspect of the present invention, the MEMS device includes a micro-cantilever beam (MCL) and is formed by etching the surface of a suitable substrate such as, for example, aluminum nitride or silicon. The excitation electronics are then preferably formed on the same substrate as the MCL to enable the beam to be operated in a vibratory mode. The excitation electronics include a transducer to provide a mechanism for vibrating the structure, a mechanism for measuring the resonant frequency of the structure, control circuitry to supervise the vibration and the detection, and a communication device or circuit to external electronics.

According to yet another aspect of the present invention, a thermoelectric chiller (TEC) module and a temperature sensor are formed in thermal contact with the MCL device. According to this aspect of the present invention, a multitude of MCL chips with respective integrated excitation circuitry can be manufactured on one substrate and then diced into individual chips. These chips are then bonded separately to TEC modules and temperature sensors so that the TEC module and temperature sensor are in thermal contact with the MCL chip.

According to yet another aspect of the invention a microelectronic deposition technology is utilized to integrate the formation of the TEC and/or the temperature sensor with the MCL. The TEC is deposited, for example, utilizing thermopiles of thermoelectric materials such as doped alloys of bismuth and telluride. The temperature sensor may also formed using a deposition technology, for example, forming a serpentine metal film of nickel or platinum to make a resistance temperature detector (RTD). Alternatively, the temperature sensor may be a semiconductor device such as a diode, transistor or thermistor.

The present invention improves the performance and reduces the complexity of the dew point sensor over prior art chilled mirror dew point hygrometers by eliminating the complex, unreliable and costly mirror/laser system. The present invention also exhibits a substantial improvement in performance over prior art sorption type sensors by eliminating reliance on the absorption of moisture in a coating, thus eliminating errors due to, for example, hysteresis which are inherent in the sorption type sensors. In addition, by integrating the control circuitry with the detector, the dew point sensor of the present invention is less costly and more reliable than the prior art. These benefits are even further amplified by integrating a thermoelectric chiller and a temperature sensor with the detector and the control circuitry, as may be provided by the present invention.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION OF THE INVENTION

The following is a detailed description of the present invention made in conjunction with the attached Figures, wherein like reference numerals will refer to like elements throughout. The present invention relates to a dew point sensor which utilizes and detects a change in mass of a structure caused by dew formed thereon to detect the dew point. The dew point sensor includes a micro-cantilever beam (MCL) which resonates at a particular frequency, wherein the frequency is a function of its mass. The temperature of the MCL is lowered by a cooling device while the resonant frequency of the beam is monitored. Once the temperature of the MCL reaches the dew point, dew forms on the beam, which changes its mass and thus alters the resonant frequency of the MCL. The change in frequency is detected and the temperature of the MCL is sensed to identify the dew point.

According to one aspect of the present invention, a thermoelectric chiller composed of a plurality of thermoelectric elements is integrated onto the MCL in order to cool the beam down to the dew point. The thermoelectric elements are preferably bismuth telluride alloys or doped semiconductor thermoelectric structures that are amenable to standard thin film processing techniques. The sensor also includes an integrated temperature sensor in thermal contact with the MCL for detecting the MCL temperature and integrated control circuitry which excites the beam into a vibratory mode and monitors the resonance and temperature of the beam.

According to another aspect of the present invention, a method of detecting the dew point is disclosed in which a MCL is excited into a vibratory mode while the temperature of the MCL is decreased. Concurrently, the resonance or vibration of the MCL is monitored and when a change in resonance or vibration is detected, the MCL temperature is identified, thereby determining the dew point. The present invention overcomes the disadvantages of the prior art chilled dew point hygrometers by eliminating costly and complex laser/mirror systems which are susceptible to contamination and errors. In addition, the present invention overcomes the disadvantages of prior art humidity sensors by eliminating the sorption coatings which corrode and exhibit hysteresis effects, thus resulting in errors.

Figure 1:
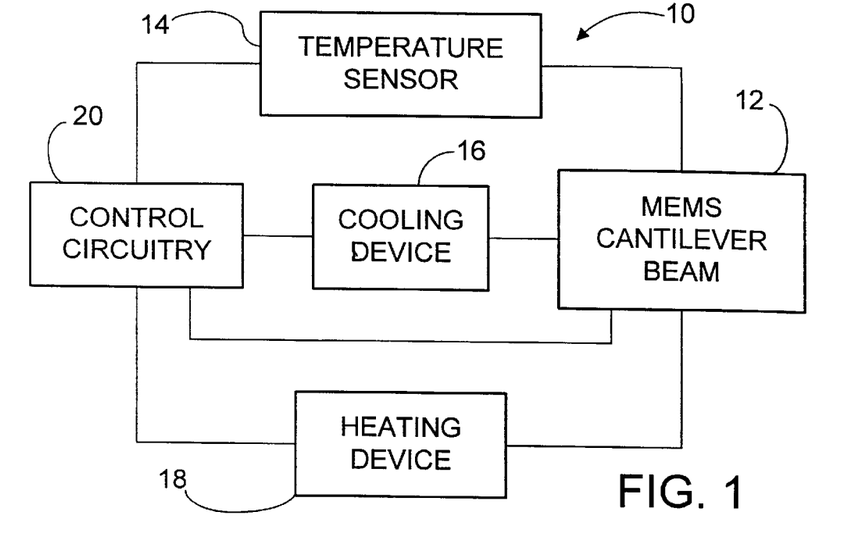
FIG. 1 is a block diagram illustrating a MEMS device dew point sensor according to the present invention.

Turning now to the Figures, FIG. 1 is a block diagram illustrating a dew point sensor 10 according to a preferred embodiment of the present invention. The sensor 10 includes a micro-electromechanical system (MEMS) device such as a micro-cantilever beam (MCL) 12. The MCL 12 is preferably formed using micro-machining processing techniques which are generally known by those skilled in the art. For example, the MCL 12 may be formed by depositing one or more films on a substrate followed by a selective etch back of the substrate to form a partially suspended cantilever beam. Alternatively, other methods may be utilized to form the structure; in addition, other structures are also considered to be micro-cantilevers and any such structure such as an etched tower which may vibrate or resonate is contemplated as falling within the scope of the present invention.

The MCL 12 preferably is coupled to a temperature sensor 14, a cooling device 16 and a heating device 18, all of which are preferably in thermal contact or thermal communication with the MCL 12. In addition, the MCL 12 is coupled to a control circuit 20 which is also coupled to the temperature sensor 14, the cooling device 16 and the heating device 18, respectively. The temperature sensor 14 may consist of any type of temperature sensing apparatus, for example, a contact thermometer, etc. In such case, any type of separate, discrete temperature sensing apparatus may be thermally coupled to the MCL 12 using, for example, a thermally conductive epoxy or a brazing or soldering process. Preferably, however, the temperature sensor 14 is integrated onto the same substrate in which the MCL 12 is built. A plurality of integrated type temperature sensors may be utilized and each such sensor is contemplated as falling within the scope of the present invention. Such exemplary integrated temperature sensors include one or more thin film thermocouples, a resistive temperature device (RTD), and a semiconductor device having known temperature performance characteristics such as a transistor, a diode or a thermistor. The temperature sensor 14 operates in conjunction with the control circuit 20 to sense the temperature at which dew is formed on the MCL 12.

The cooling device 16 is also in thermal contact with the MCL 12 and operates to cool the MCL 12 down to the dew point. The cooling device may be a separate, discrete component such as a commercial thermoelectric chiller (e.g., part no. OT1.2-18-F2, manufactured by Melcor, Inc. or part no. M1021T manufactured by Marlow, Inc.) or any other type of chilling device. In such a case, the discrete cooling device 16 is placed in thermal communication with the MCL 12 using, for example, a thermally conductive epoxy to effectuate an efficient cooling of the MCL 12 and thereby conserve power. Preferably, however, the cooling device 16 is integrated onto the same substrate on which the MCL 12 is formed. Even more preferably, the cooling device 16 is integrated onto the MCL 12 and consists of a plurality of thermoelectric materials to form cold junctions of peltier thermoelements using thin film processing techniques as will be described in greater detail infra. The cooling device 16 operates in conjunction with the control circuit 20 to initiate and discontinue the cooling of the MCL 12 as desired.

The heating device 18 is an optional component in the dew point sensor 10 of FIG. 1. The heating device 18 operates to deliver heat to the MCL 12 once the MCL 12 has reached the dew point to thereby elevate the MCL 12 above the dew point and cause the dew to efficiently evaporate. Therefore the heating device 18 permits the dew point sensor 10 to be repeatedly and rapidly temperature cycled when used in conjunction with the cooling device 16 for the collection of multiple dew point measurements. Alternatively, the dew point sensor 10 may operate without the heating device 18 by simply discontinuing the cooling of the MCL 12 and allowing the ambient environment temperature to elevate the MCL 12 temperature above the dew point which results in the evaporation of dew from the MCL 12 after the dew point has been reached.

The heating device 18 may include any form of heating apparatus and any such heating mechanism is contemplated as falling within the scope of the present invention. Exemplary heating devices include an electro-thermal heater or a thermoelectric chiller (TEC) running in a reverse mode (e.g., reverse current) to produce heating rather than cooling. Preferably, the heating device 18 is integrated on the substrate on which the MCL 12 is constructed. More preferably, the heating device 18 is formed on the MCL 12 in order to most efficiently heat the MCL and drive the moisture off the beam once the dew point is detected. Exemplary integrated structures include a resistor, a TEC running with reverse current or any other structure or semiconductor device that dissipates heat.

The control circuit 20 is preferably coupled to each of the sensor components and provides at least the following control functions. The control circuit 20 excites the MCL 12 into a vibratory mode, wherein the vibration or resonance of the MCL 12 is a function of its mass. According to one exemplary embodiment of the present invention, the excitation is initiated by applying a voltage signal across a piezoelectric film associated with the MCL 12, as will be discussed in greater detail infra. Alternative methods of exciting the MCL 12 into a vibratory mode, however, may also be utilized and any such mechanism is contemplated as falling within the scope of the present invention. For example, resonance or vibration of the MCL 12 may be initiated by forming an electrode below the MCL 12 and applying a DC voltage thereto and then applying an AC voltage to the MCL 12 which is centered about the DC voltage. The time-varying charge on the MCL 12 will then cause the MCL 12 to vibrate at a frequency established by the AC voltage frequency. Once the resonance is sufficiently stabilized, the control circuit 20 detects the resonance of the MCL 12. The detection of the vibration or resonant frequency may be accomplished in many ways. For example, another electrode may be formed in the substrate below the MCL 12 to form a bottom plate of a capacitor, wherein the top plate of the capacitor is formed by the MCL 12. As the MCL 12 vibrates, the spacing between the capacitor plates varies in accordance with the vibration frequency, thus creating a time-varying capacitance (C(t)) which may be utilized in conjunction with decoding circuitry to determine the actual vibration frequency of the MCL 12. Alternatively, a piezoelectric material may be attached to the MCL 12 in such a manner that the vibration of the MCL 12 deforms the piezoelectric material and results in a time-varying voltage which correlates to the vibration frequency of the MCL 12. In yet another alternative, a bridge circuit may be utilized, wherein the circuit output signal will change in response to a change in vibration of the MCL 12, thus allowing the dew point to be detected.

Any excitation and detection circuitry or methods may be utilized within the control circuitry 20 and such alternatives are contemplated as falling within the scope of the present invention. Additional exemplary excitation and detection circuitry and methods are disclosed in U.S. Pat. Nos. 5,275,055 and 5,772,322 which are hereby incorporated by reference in their entirety.

Preferably, once the initial MCL resonance is detected by the control circuit 20, the control circuit 20 activates the cooling device 16 to begin cooling the MCL 12 down toward the dew point. As the cooling device 16 cools the MCL 12, the control circuit 20 continues to monitor the resonance of the MCL 12. Once the MCL 12 reaches the dew point, dew forms on the beam, thus changing the effective mass of the MCL 12. Since the resonance or vibration frequency of the MCL 12 is a function of its mass, the formation of dew on the beam changes the resonant or vibration frequency of the MCL 12. Once the control circuit 20 detects the change in resonance or vibration (preferably a change in resonance or vibration greater than a predetermined amount for a predetermined time to avoid detection errors due to noise), the control circuit 20 activates the temperature sensor 14 to determine the temperature at which the dew forms, thus identifying the dew point.

According to one exemplary embodiment of the present invention, the control circuit 20 activates the temperature sensor 14 once the change in the MCL resonance is detected. Alternatively, however, the temperature sensor 14 may be measuring the temperature of the MCL 12 continuously and reporting the detected temperature to the control circuit 20 on a continuous basis, wherein the detected temperature is then stored in a memory within the control circuit 20 once the change in the MCL resonance is detected.

The control circuit 20 also controls the heating device 18 and activates the heating device 18 after the temperature of the MCL 12, at the time its resonance changes, is detected by the temperature sensor 14 and communicated to the control circuit 20. The heating device 18 applies heat to the MCL 12 to rapidly raise the temperature of the MCL 12 above the dew point and evaporate the dew which had formed on the MCL 12. Once the heating device 18 has been activated for a predetermined time (or alternatively until the initial resonance is detected) in order to evaporate the dew on the MCL 12, the control circuit 20 deactivates the heating device 18 and either re-activates the cooling device 16 to repeat the dew point detection sequence or discontinues the control process. If multiple detection sequences are performed, the control circuit 20 saves each dew point temperature in a memory location, wherein the multiple data points then may be used to provide statistical data such as the average dew point temperature, the median dew point temperature, the standard deviation and other statistical quantities as may be desired.

The control circuit 20 may operate as a separate, discrete circuit such as a programmable logic controller which is wire bonded to the various components 12, 14, 16 and 18. Alternatively, the control circuit 20 may be bonded to the other integrated components in a flip-chip type arrangement using solder balls as is well known by those skilled in the art. In yet another alternative embodiment of the present invention, the control circuit 20 is integrated onto the same substrate as the MCL 12 and the other components are formed using conventional semiconductor processing techniques, thus integrating the entire sensor 10 onto a single substrate. In this manner, multiple sensors may be manufactured simultaneously on a single wafer, thereby reducing the cost and improving the reliability of the dew point sensor.

Figure 2:
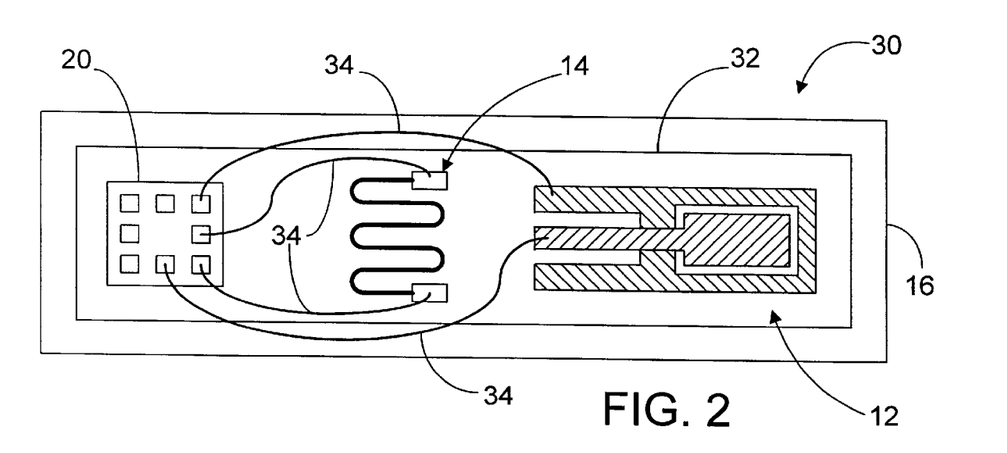
FIG. 2 is a top or plan view of a dew point sensor having a control circuitry block bonded to a MEMS device which is integrated with a temperature sensor according to the present invention.
Figure 3:
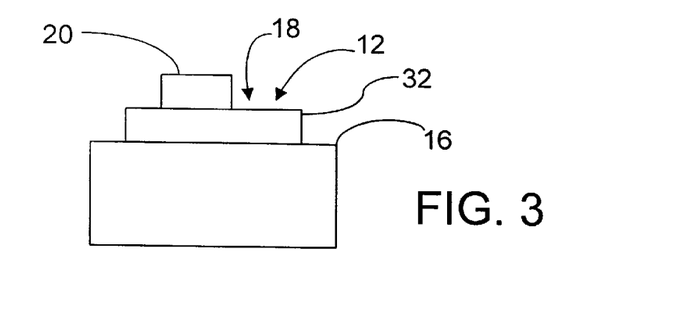
FIG. 3 is a side view of the dew point sensor of FIG. 2 according to the present invention.

A top or plan view of a dew point sensor 30 according to the present invention is illustrated in FIG. 2 with its corresponding cross section in FIG. 3 (not shown to scale). In FIGS. 2 and 3, the sensor 30 includes the MCL 12 which is shown formed on a substrate 32 having a resistive temperature device (RTD) type temperature sensor 14 formed thereon. As is well known by those skilled in the art, an RTD 14 is a resistance which is dependent upon or a function of temperature. That is, the RTD 14 has a known and well characterized temperature coefficient. Therefore by forcing a constant current through the RTD 14 and detecting the voltage across the structure, the measured voltage is correlated to a resistance value which reflects the temperature at the RTD 14. In the above manner, the RTD 14 can easily detect the temperature. Since it is desirable to detect the temperature of the MCL 12 as accurately as possible, it is preferable for the temperature sensor 14 to be positioned on or near the MCL 12 to avoid errors due to temperature gradients caused by thermal dissipation into the substrate 32.

As further illustrated in FIGS. 2 and 3, the control circuit 20 is a discrete circuit which is bonded to the substrate 32 and electrically coupled to the MCL 12 and the temperature sensor 14 via wire bonding 34. Alternatively, however, as discussed supra, the control circuit 20 may be formed, via conventional semiconductor processing techniques, on and/or in the substrate 32. The entire substrate 32 is then coupled to a cooling device 16, for example, a commercially available thermoelectric chiller (e.g., part no. OT1.2-18-F2 manufactured by Melcor, Inc.) which is preferably coupled to the substrate 32 using, for example, a thermally conductive paste or epoxy.

Figure 4:
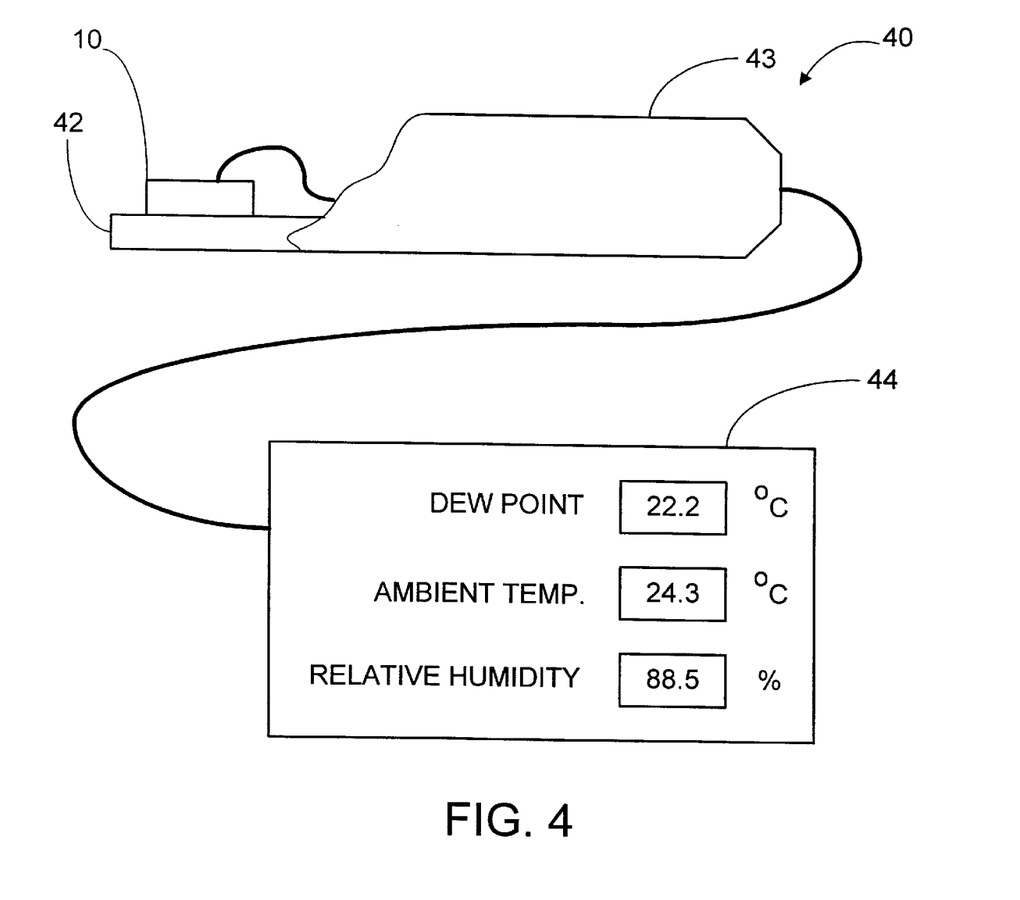
FIG. 4 is a system level diagram illustrating a MEMS device dew point sensor coupled to conversion and display circuitry according to the present invention.

Once the sensor 10 construction is completed, the sensor 10 is incorporated into a dew point detection system 40 as illustrated in FIG. 4. The sensor 10 is preferably placed on a supporting substrate 42 covered by a protective cover 43 to minimize external noise components from adversely impacting the dew point measurements. The protective cover is preferably constructed with one or more holes for maintaining the environment inside the cover 43 substantially the same as the external environment to ensure an accurate sample. The sensor 10 is then bonded or otherwise coupled to an electrical connector within the cover 43 (not shown) for transmitting the detected dew point temperature to a conversion and display circuit 44 having display driver circuitry for displaying the detected dew point in a manner which is easy to view. In addition, the conversion and display circuit 44 may also include a processor and a temperature sensor (not shown) for detecting the ambient environment temperature and using the dew point temperature and ambient temperature for calculating the relative humidity according to, for example, the following formula:

$$RH=\{(D+273.2)/(T+273.2)\}^{-4.928} \times \exp\{-6763[(1/(D+273.2)-1/(T+273.2)]\} \times 100,$$

wherein RH is the relative humidity, D is the detected dew point temperature and T is the ambient temperature, respectively. The conversion and display circuit 44 preferably then is operable to display the ambient temperature and the relative humidity in a manner which is easy to view.

Figure 5A:
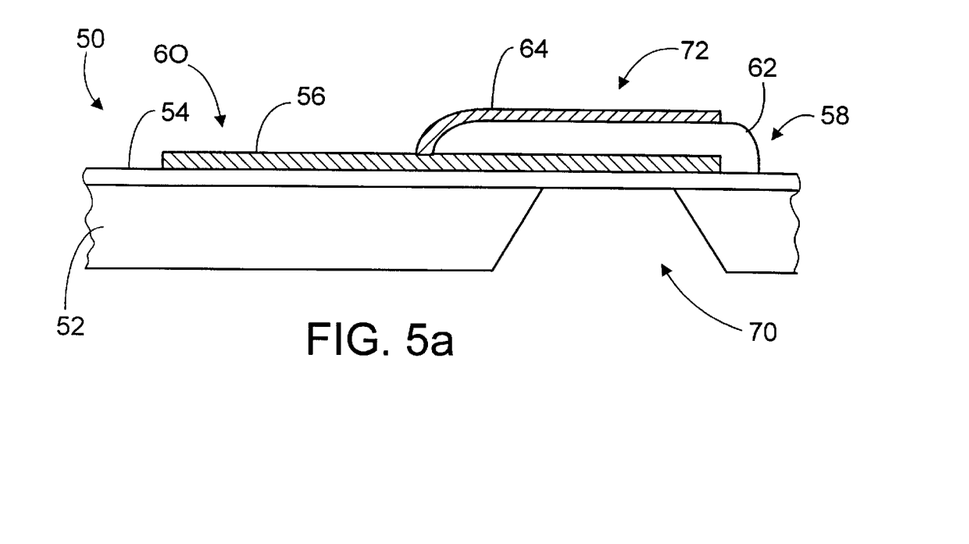
FIG. 5a is a fragmentary cross section diagram illustrating a MEMS device having an etch pit according to the present invention.
Figure 5B:
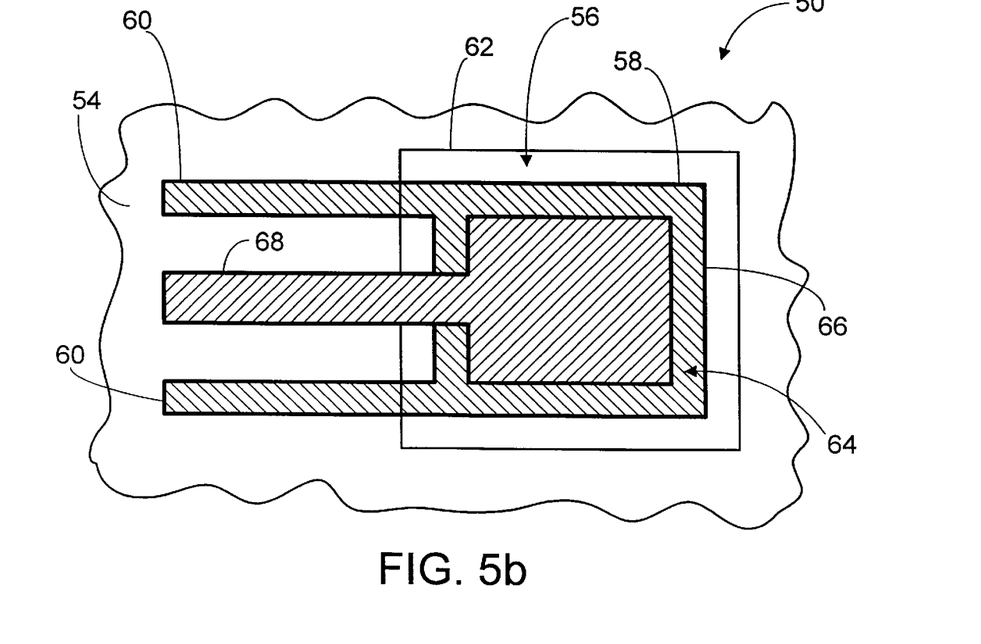
FIG. 5b is a fragmentary top view of the MEMS device of FIG. 5a according to the present invention.

As discussed supra, the MCL 12 may consist of a MEMS type device formed by micro-machining. The MCL 12 may be formed using various structures and each such structure is contemplated as falling within the scope of the present invention. FIGS. 5a and 5b illustrate a cross section view and a top or plan view, respectively, of one exemplary MCL structure 50. The MCL structure 50 includes a substrate 52 such as silicon, however, other materials may also be used, for example, aluminum nitride, quartz or a ceramic. The substrate 52 is preferably covered with an insulating layer 54, preferably a thermal oxide such as silicon dioxide having a preferred thickness of about 2,500 Angstroms which functions as an electrically insulating layer and an etch stop as will be discussed in greater detail below. A first conductive layer 56, preferably a metal, for example, aluminum, is formed on the insulating layer 54 and is patterned to form an electrode portion 58 and one or more contact portions 60 for connection to the control circuit 20 (via either wire bonding, flip-chip connections or semiconductor processing interconnect metallization), as illustrated in FIG. 5b.

Once the first conductive layer 56 is formed and patterned, a piezoelectric layer 62 is formed on the first conductive layer 56 and patterned to substantially cover the electrode portion 58 of the first conductive layer 56. The piezoelectric layer 62 exhibits deformations which are a function of a voltage applied to the layer 62. It is this characteristic of the piezoelectric layer 62 which is utilized to vibrate the MCL structure 50 according to one embodiment of the present invention. The piezoelectric layer 62 may consist of aluminum nitride having a thickness in the range of about 0.2 microns to about 10 microns and most preferably about 1–2 microns. Alternatively, however, other piezoelectric materials may be utilized such as lead zirconia titanate (pZT), zinc oxide (ZnO), etc. A second conductive layer 64 is then formed over the piezoelectric layer 62 and patterned to form an electrode portion 66 and a contact portion 68 in a manner similar to the first conductive layer 56. The first and second conductive layers 56 and 64 sandwich the piezoelectric layer 62 with their electrode portions 58 and 66, respectively, and generate voltage potentials across the piezoelectric layer 62 according to electrical signals applied to the contact portions 60 and 68 from the control circuit 20, which generate the piezoelectric deformations for exciting the MCL structure 50 into a vibratory mode.

Lastly, the MCL structure 50 has an etch pit 70 in the substrate 52 in a position that underlies at least a portion of the electrode regions 58 and 66. The etch pit 70 is formed by a back etch of the substrate 52 using a selective etch, wherein the insulating layer 52 serves as an etch stop. The etch pit 70 removes a substantial amount of mass from the substrate 52 in a region local to the electrode regions 58 and 66 to form a beam portion 72 of the MCL structure 50. This reduction in mass increases the sensitivity of the MCL structure 50 since the subsequent formation of dew on the beam portion 72 results in a greater change in the mass of the structure 50 and thus exhibits a greater change in its resonance as a result of the formation of dew.

Figure 6A:
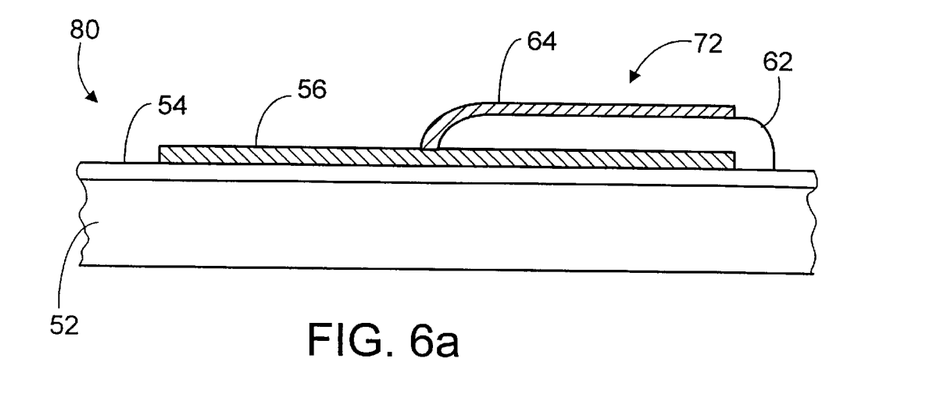
FIG. 6a is a fragmentary cross section diagram illustrating a MEMS device without an etch pit according to the present invention.
Figure 6B:
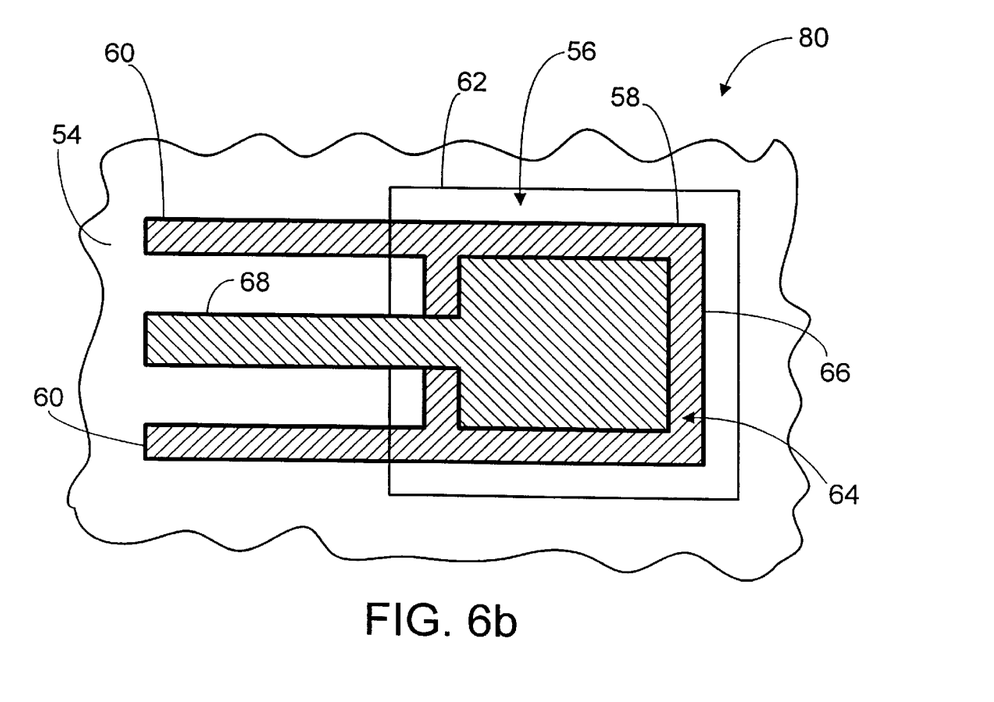
FIG. 6b is a fragmentary top view of the MEMS device of FIG. 6a according to the present invention.

The MCL structure 50 of FIG. 5a incorporates an etch pit 70; alternatively, however, an entire portion of the substrate 52 may be removed, thereby leaving the beam portion 72 supported only at an end near the contact regions 60 and 68 to further improve the sensitivity of the structure. In yet another alternative embodiment of the present invention, as illustrated in FIGS. 6a and 6b, the etch step which forms the etch pit 70 may be skipped. Accordingly, the MCL structure 80 of FIG. 6a has a greater mass at the beam portion 72 and thus has a lower sensitivity, wherein the piezoelectric layer 62 vibrates the beam portion 72 primarily in a planar mode. Without the etch pit 70, the structure 80 has decreased complexity due to its simplified construction. According to the present invention, various types of MCL structures having differing sensitivities may be utilized in accordance with the type of application desired.

Figure 7A:
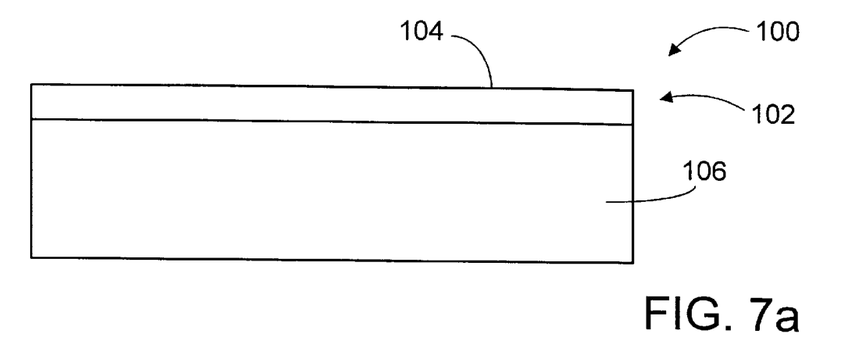
FIGS. 7a–7f are cross section diagrams illustrating a method of forming a MEMS device for a dew point sensor according to the present invention.
Figure 7B:
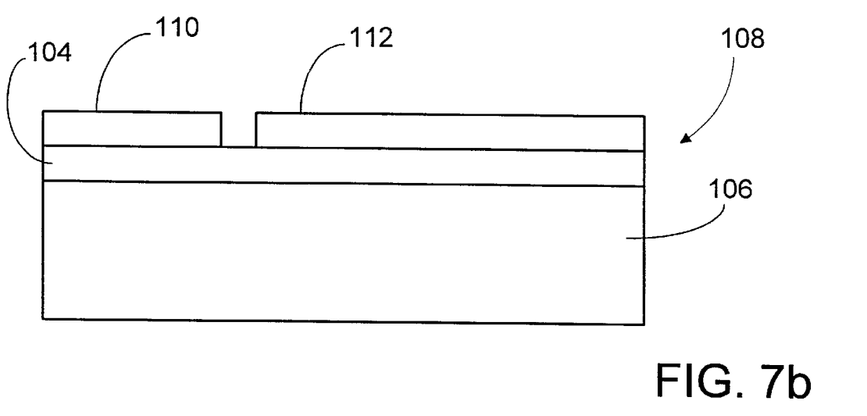
Figure 7C:
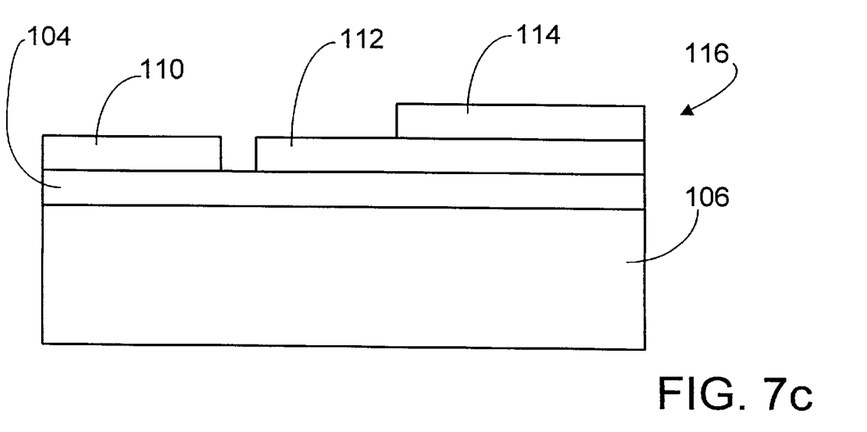

A method 100 of forming an exemplary MCL structure 12 integrated with the temperature sensor 14 as illustrated in FIGS. 1 and 2 is illustrated in detail in a plurality of cross section diagrams, FIGS. 7a–7f. In FIG. 7a, the method 100 begins at step 102 by forming an insulating layer 104 such as silicon dioxide having a preferred thickness range of about 2,000 Angstroms to about 10,000 Angstroms (and most preferably about 5,000 Angstroms) on a silicon substrate 106 using, for example, a thermal oxidation process. As illustrated in FIG. 7b, the method 100 continues at step 108 by depositing a conductive layer having a thickness of about 0.2 microns via, for example, sputtering or chemical vapor deposition (CVD) and patterning the layer into two regions 110 and 112. The patterning is preferably performed using an etch process, for example a wet etch or a dry plasma etch, as is well known by those skilled in the art. One of the two regions include a temperature sensor region 110, wherein the conductive layer is etched to form, for example, a serpentine pattern resistive temperature device. The other of the two regions includes an MCL portion 112 having a contact portion and an electrode portion as illustrated in FIGS. 5a, 5b, 6a and 6b.

Figure 7D:
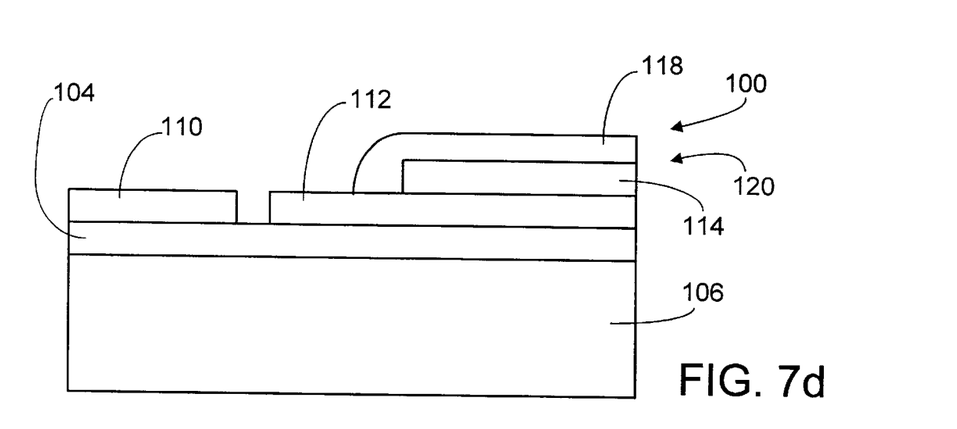

After the formation of the first patterned conductive layer, a piezoelectric material 114 such as aluminum nitride ($Al_3N_4$) is deposited and patterned over the electrode portion of the conductive region 112 at step 116, wherein the piezoelectric layer 114 preferably has a thickness of about 0.2 microns to about 10 microns and most preferably about 1–2 microns. A second conductive layer is then deposited and patterned to form a second, upper electrode region 118 at step 120 having a preferred thickness of about 0.2 microns as illustrated in FIG. 7d. Note that the first and second conductive layers 112 and 118 do not contact one another; rather, the layers 112 and 118 are laterally displaced from one another. Although in the above exemplary embodiment, the first conductive layer 112 is used to form the temperature sensor region 110, the second conductive layer 118 may alternatively be used by altering the patterning process as is well known by those skilled in the art. In yet another alternative embodiment, a separate, third conductive layer may be deposited and patterned to form the temperature sensor portion 110. The second conductive portion 118 has a contact portion and an electrode portion similar to that illustrated in FIGS. 5a, 5b, 6a and 6b.

Figure 7E:
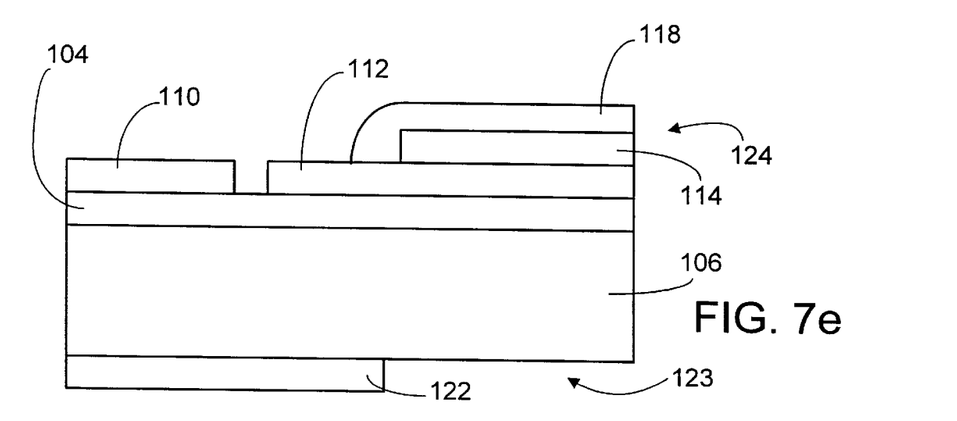
Figure 7F:
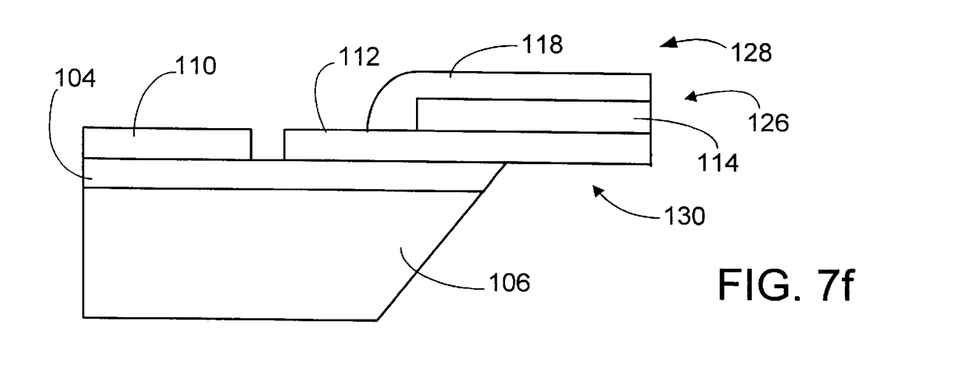

Once the second electrode portion 118 is formed at step 120, a photoresist material 122 is deposited and patterned on a bottom portion of the substrate 106 to expose a portion 123 of the substrate 106 corresponding to the electrode portions of the MCL structure. A back etch is then performed at step 126, wherein the insulating layer 104 acts as an etch stop to thereby form a beam 128. A second etch is then preferably performed to remove the exposed insulating region 130 to thereby further reduce the mass of the beam which results in an increase in sensitivity of the structure.

As discussed supra, the dew point sensor 10 of the present invention as illustrated in FIG. 1 may be constructed as a plurality of discrete components as illustrated in FIGS. 2 and 3 or alternatively may be integrated together onto a single substrate which allows for the miniaturization of the dew point sensor 10 along with a reduction in cost and improved reliability. An integrated dew point sensor having a combined heating device and cooling device integrated within the MCL is provided in conjunction with FIGS. 8a–15. According to this exemplary embodiment of the present invention, the combined heating device and cooling device is formed using a plurality of judiciously positioned thermoelements coupled together in series to form a plurality of junctions on the beam of the MCL structure. The thermoelements are coupled to the control circuit 20 and when a current is forced through the thermoelements in a first direction, the junctions overlying the beam portion of the MCL structure cool the beam down toward the dew point via the peltier effect. In addition, when the thermoelements have a current forced through them in the opposite direction, the junctions overlying the beam portion heat up, and raise the beam portion of the MCL structure above the dew point and evaporate the dew off the beam, again via the peltier effect.

Figure 8A:
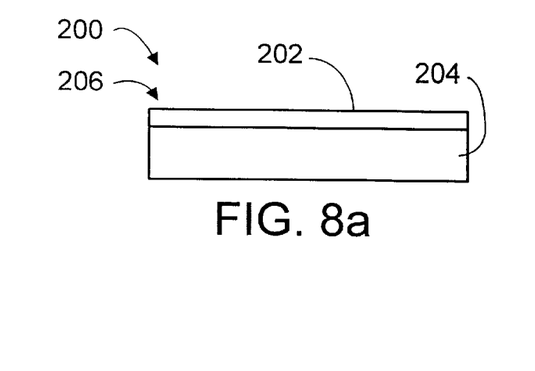
FIG. 8a is a cross section of a substrate having an insulating layer formed thereon according to the present invention.
Figure 15:
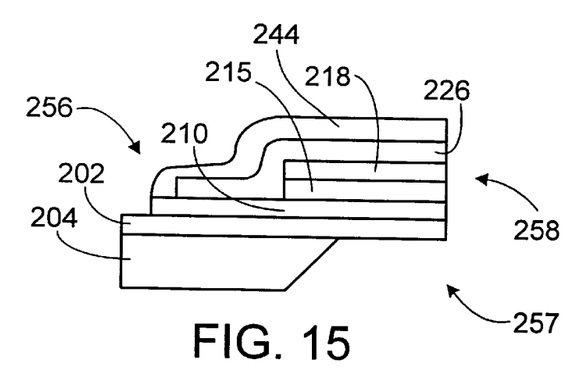
FIG. 15 is a cross section diagram similar to FIG. 14a, having a portion of the substrate etched to complete the formation of a micro-cantilever beam according to the present invention.

As is well known by those skilled in the art, the peltier effect may be described as the liberation or absorption of heat when an electric current flows across a junction of two dissimilar conductors. More particularly, the peltier effect is defined as the reversible change in heat content when one coulomb crosses the junction of dissimilar conductors and may be expressed as:

$$\Delta Q = I^*(dE_{ab}/dT)^*T,$$

wherein $\Delta Q$ is heat transfer, I is the electric current, $E_{ab}$ is the electric power between two points A and B, and T is the temperature. As can be seen from the above equation, $\Delta Q$ may be positive or negative so that the thermoelements may operate as a chiller or as a heater. Thermoelectric materials are optimized based on one of several figures of merit, which may be characterized as:

$$Z = S^2(\sigma/k),$$

wherein S is the thermoelectric power, $\sigma$ is the electrical conductivity of the thermoelements, and K is the thermal conductivity of the thermoelements. Further details of the integrated dew point sensor will be discussed in conjunction with FIGS. 8a–15.

Figure 8B:
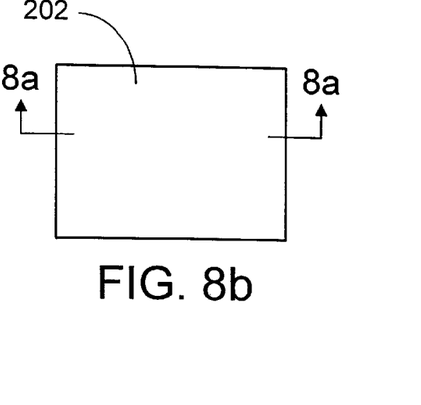
FIG. 8b is a top or plan view of FIG. 8a according to the present invention.
Figure 9A:
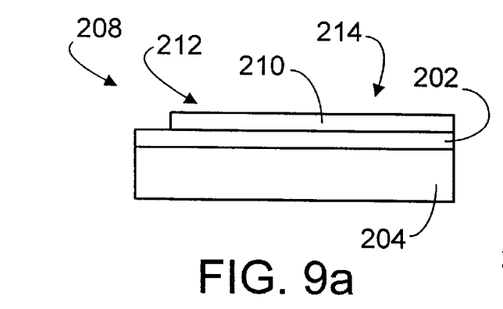
FIG. 9a is a cross section similar to FIG. 8a, having a first conductive material formed on the insulating layer according to the present invention.
Figure 9B:
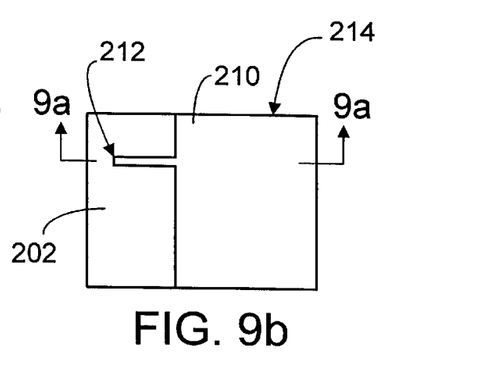
FIG. 9b is a top or plan view of FIG. 9a according to the present invention.

In the method 200 of FIGS. 8a–5 only the MCL structure, temperature sensor and heating/cooling device are illustrated. It should be understood, however, that the control circuit 20 is integrated with these components on the substrate according to standard semiconductor processing techniques. In FIG. 8a, an insulating layer 202 is formed on a substrate 204 such as silicon across the entire portion of the substrate 204 which does not contain the control circuitry at step 206, as illustrated in FIG. 8b. In FIG. 9a, the method 200 continues at step 208, wherein a first conductive layer 210 is formed and patterned to form a contact portion 212 for interconnecting with the control circuit 20 and an electrode portion 214 which will be used to excite the MCL structure into a vibratory mode, as illustrated in FIG. 9b.

Figure 10A:
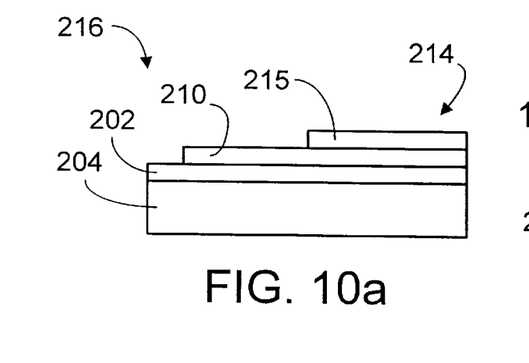
FIG. 10a is a cross section similar to FIG. 9a, having a piezoelectric material formed on the conductive layer according to the present invention.
Figure 10B:
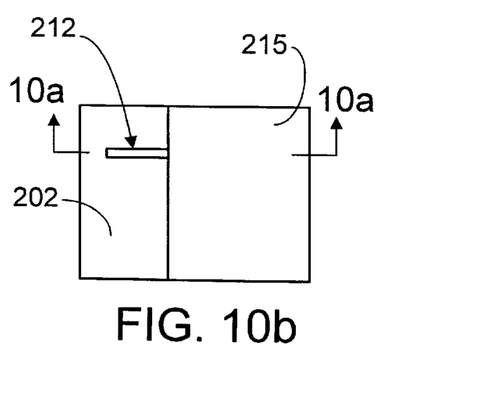
FIG. 10b is a top or plan view of FIG. 10a according to the present invention.
Figure 11A:
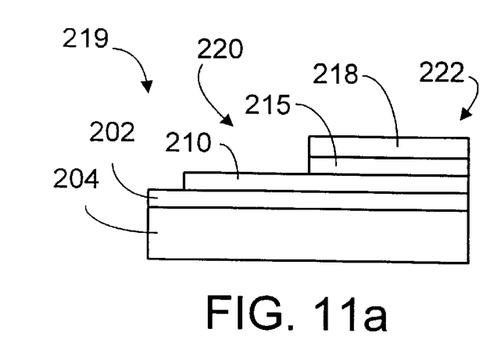
FIG. 11a is a cross section similar to FIG. 10a, having a second conductive material formed on the piezoelectric material according to the present invention.
Figure 11B:
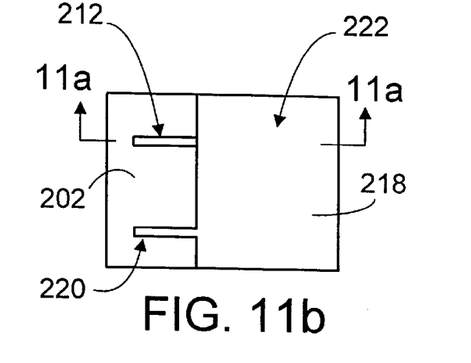
FIG. 11b is a top or plan view of FIG. 11a according to the present invention.

After the formation and patterning of the first conductive layer 210 at step 208, a piezoelectric film 215, for example, aluminum nitride ($Al_3N_4$) is deposited and patterned at step 216 to thereby substantially overlie the electrode portion 214 of the first conductive layer 210, as illustrated in FIGS. 10a and 10b. Subsequently, a second conductive layer 218 is deposited and patterned at step 219, as illustrated in FIGS. 11a and 11b, to form a contact portion 220 for connection to the control circuit 20 which is laterally spaced from the contact portion 212 of the first conductive layer 210 to maintain the regions electrically isolated from one another. The second conductive layer 218 also includes an electrode portion 222 which substantially overlies the piezoelectric layer 215, thereby sandwiching the piezoelectric layer 215 between two conductive electrodes.

The first and second conductive layers 210 and 218 are coupled to the control circuit 20 via the contact portions 212 and 220 (not shown) to transmit electric signals to the electrode portions 214 and 222. The resulting voltage which develops across the electrodes 214 and 222 causes a deformation in the piezoelectric layer 215 which causes the MCL structure to resonate.

Figure 12A:
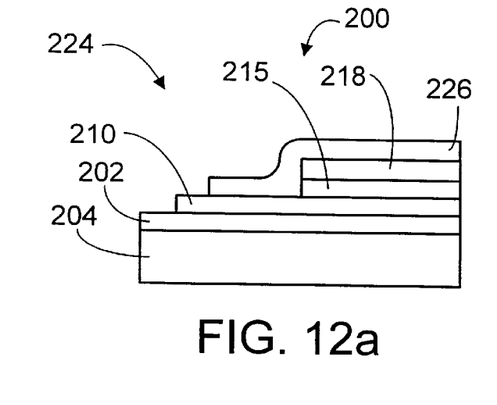
FIG. 12a is a cross section similar to FIG. 11a, having an isolation layer formed on the second conductive material according to the present invention.
Figure 12B:
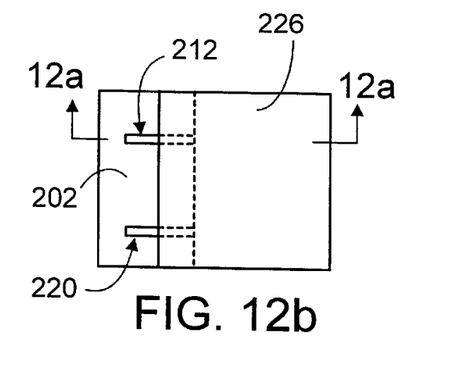
FIG. 12b is a top or plan view of FIG. 12a according to the present invention.

After the electrodes are completed at step 219, the method 200 continues at step 224, wherein an isolation layer 226 is formed over the second conductive layer 218 and over a portion of the exposed insulating layer 202, as illustrated in FIGS. 12a and 12b. The isolation layer 226 provides both electrical isolation and thermal isolation for the subsequent structures to be formed thereon. The electrical isolation will prevent the control signals sent from the control circuit 20 to the electrodes 214 and 222 from interfering with the thermoelements which will be subsequently formed on top of the isolation layer 226. The isolation layer 226 further provides a lateral thermal isolation so that minimal heat transfer occurs horizontally while substantially allowing the heat or cold to transfer vertically down to the beam structure. Preferably, the isolation layer 226 is a thin layer (e.g., about 2,500 Angstroms) of silicon carbide, however, other materials such as alumina, TiN, glass (e.g., BpSG (borophosphate silica glass or a spin-on glass) may also be utilized.

Figure 13A:
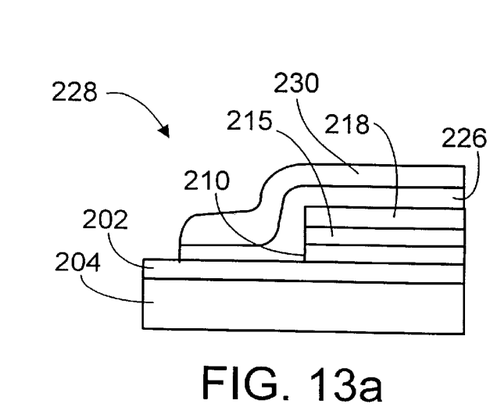
FIG. 13a is a cross section diagram similar to FIG. 12, having a plurality of thermoelectric materials formed on the insulating layer according to the present invention.
Figure 13B:
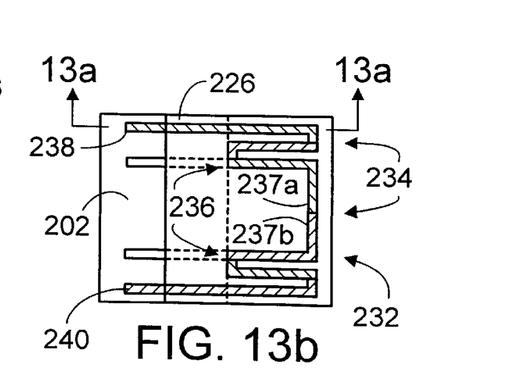
FIG. 13b is a top or plan view of FIG. 13a according to the present invention.

The method 200 continues at step 228, wherein a layer of thermoelectric material 230, for example, a bismuth telluride alloy, is deposited and patterned to form a plurality of separate structures called thermoelements 232 which are connected together in series at junctions 234 and 236, as illustrated in FIGS. 13a and 13b. Preferably, the thermoelectric materials are formed by depositing a thermoelectric material and selectively doping various regions to form p-type and n-type thermoelectric materials 237a and 237b, respectively. The doping step is preferably performed in the same manner as conventional doping in semiconductor manufacturing and the n-type and the p-type dopants may vary depending upon the thermoelectric materials being employed. For example, if semiconductor thermoelectric materials are utilized, boron or phosphorous may be used or in the case of bismuth telluride alloys, an exemplary dopant may be copper bromide (CuBr).

The thermoelements 232 are preferably configured so that the first junctions 234 are on the beam portion which corresponds to the electrode regions to cool down the beam to the dew point. In addition, it is preferred that the thermoelements be configured so that the second junctions 236 are located further away from the beam where the mass is greater and the heat is more easily dissipated vertically down to the substrate 204.

Each end 238 and 240 of the series connected thermoelements 232 are connected to the control circuit 20 (not shown) for initiation of the thermoelectric device. When the control circuit 20 forces current through the thermoelements 232 in a first direction, the junctions 234 (previously called the first junctions) are cold, wherein heat is pumped laterally away from the beam and then dissipated vertically into the substrate 204 which operates as a heat sink. Alternatively, when the control circuit 20 forces current through the thermoelements 232 in the opposite direction, the junctions 234 are hot junctions which elevate the temperature of the beam above the dew point and evaporate the dew away while the junctions 236 are hot junctions. In the above manner, the control circuit 20 can dictate whether the thermoelements 232 behave as a heating device or a cooling device based on the direction in which current is driven through the thermoelements 232. Therefore the present invention advantageously integrates the cooling device 16 and the heating device 18 of FIG. 1 together to further miniaturize and simplify the dew point sensor 10.

Figure 14A:
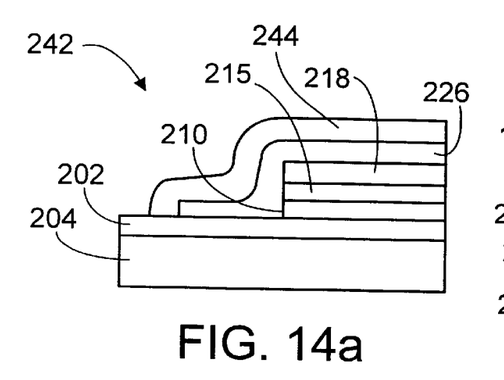
FIG. 14a is a cross section diagram similar to FIG. 13a, having a temperature sensing layer formed on the insulating layer according to the present invention.
Figure 14B:
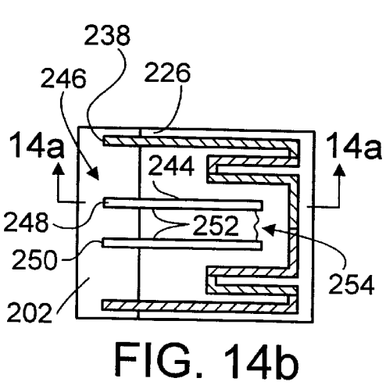
FIG. 14b is a top or plan view of FIG. 14a according to the present invention.

At step 242, the thermoelements 232 are masked and another conductive layer 244, for example, platinum or nickel, is deposited and patterned to form a temperature sensor, for example, a resistive temperature device (RTD) 246, on the electrode portions, as illustrated in FIGS. 14a and 14b. Alternatively, however, other type thin film temperature sensors may be constructed and are contemplated as falling within the scope of the present invention, such as a thermocouple, a transistor, a thermistor, etc. In the present exemplary embodiment, the RTD 246 has each end 248 and 250 coupled to the control circuit 20 (not shown) so that the control circuit 20 can force a constant current and detect the voltage between the ends 248 and 250 which indicates the resistance of the device 246 and therefore the temperature of the beam. Preferably, the leads 252 of the RTD 246 are substantially thicker than a detection portion 254 so that the resistance of the leads 252 is substantially negligible.

Lastly, the method 200 preferably concludes at step 256, wherein the substrate 204 is etched in a region 257 under the electrode portions of the first and second conductive layers 210 and 218 to form the beam 258. In the above exemplary method 200, a dew point sensor 10 integrates the control circuit 20, the MCL structure 258, the temperature sensor 246 and the heating/cooling device 232 onto a single substrate 204, thus greatly simplifying the construction and improving the performance of the sensor and substantially reducing the size and the cost of the sensor over prior art devices.

In the exemplary embodiments of the present invention, the piezoelectric film was illustrated sandwiched vertically by the electrodes. Alternatively, the piezoelectric film may be sandwiched by the electrodes horizontally as may be desired. In addition, silicon carbide was disclosed as an exemplary isolation material to allow the cold junctions over the beam to chill easily while allowing heat to be dumped from the hot junctions into the underlying substrate for maximum efficiency. Alternatively, however, some isotropic materials which exhibit thermal properties which vary with respect to their crystal direction may be utilized, for example, single crystal diamond or diamond-like carbon.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described components (assemblies, devices, circuits, etc.), the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more other features of the other embodiments as may be desired and advantageous for any given or particular application.

What is claimed is:

1. A dew point sensor, comprising:

a micro-cantilever beam formed on a substrate;

a cooling device in thermal contact with the micro-cantilever beam;

a temperature sensor in thermal contact with the micro-cantilever beam; and a control circuit coupled to the micro-cantilever beam, the cooling device and the temperature sensor, wherein the control circuit is operable to monitor a resonance of the micro-cantilever beam, control a temperature of the cooling device and receive a temperature indication from the temperature sensor, thereby identifying the temperature of the micro-cantilever beam when the resonance of the micro-cantilever beam changes due to a change in mass caused by dew on the micro-cantilever beam when the dew point is reached.

2. The dew point sensor of claim 1, further comprising a heating device in thermal contact with the micro-cantilever beam, thereby providing for a temperature cycling of the micro-cantilever beam in response to the control circuit.

3. The dew point sensor of claim 1, further comprising a conversion circuit for converting a dew point temperature to relative humidity.

4. The dew point sensor of claim 1, wherein the cooling device comprises a thermoelectric chiller.

5. The dew point sensor of claim 1, wherein the temperature sensor is integrated with the micro-cantilever beam on the substrate.

6. The dew point sensor of claim 5, wherein the temperature sensor includes one of a resistive temperature device, a thermocouple and a semiconductor device.

7. The dew point sensor of claim 1, wherein the control circuitry is integrated with the micro-cantilever beam on the substrate.

8. The dew point sensor of claim 1, wherein the micro-cantilever beam comprises a pair of opposing electrodes having a piezoelectric material therebetween and wherein the micro-cantilever beam vibrates at a frequency dictated by a voltage potential across the electrodes.

9. The dew point sensor of claim 8, wherein a portion of the substrate under the pair of electrodes is etched away, thereby providing improved sensitivity in the resonance of the micro-cantilever beam.

10. The dew point sensor of claim 9, further comprising an insulating layer between the pair of electrodes and the substrate, and wherein the insulating layer forms an etch stop for the removal of the portion of the substrate under the pair of electrodes.

11. The dew point sensor of claim 8, wherein the cooling device comprises a thermoelectric chiller and is integrated with the micro-cantilever beam on the substrate.

12. A dew piont sensor comprising:

a micro-cantilever beam formed on a sustrate;

a cooling device in thermal contact with the micro-cantilever beam; and a control circuit coupled to the micro-device beam, the cooling device and the temperature sensor, wherein the control circuit is operable to monitor a resonance of the micro-cantilever beam, control a temperature of the cooling device and receive a temperature indication from the temperature sensor, thereby identifying the temperature of the micro-cantilever beam when the resonance of the micro-cantilever beam changes due to a change in mass caused by dew on the micro-cantilever beam when the dew point is reached;

wherein the micro-cantilever beam vibrates at a frequency dictated by a voltage potential across the electrodes;

the cooling device comprises a thermoelectric chiller and is integrated with the micro-cantilever beam on the substrate; and wherein the thermoelectric chiller is formed on the micro-cantilever beam, wherein the thermoelectric chiller comprises;

an insulating layer formed on the micro-cantilever beam; and a plurality of thermoelectric structures formed of two types of material, and wherein alternating material type thermoelectric structures contact one another forming a cold junction adjacent a first end of the micro-cantilever beam and a hot junction adjacent a second end of the micro-cantilever beam at end.

13. The dew point sensor of claim 12, wherein the cold junctions are positioned over at least a portion of the micro-cantilever beam for lowering a temperature of the micro-cantilever beam to the dew point.

14. The dew point sensor of claim 12, wherein the plurality of structures comprise doped bismuth telluride alloys or doped semiconductor thermoelectric materials.

15. A method of determining the dew point, comprising the steps of:

exciting a micro-cantilever beam in a vibratory mode;

decreasing a temperature of the micro-cantilever beam, wherein when the temperature reaches the dew point, dew forms on the micro-cantilever beam and changes the mass of the micro-cantilever beam which causes a resonance of the micro-cantilever beam to change; and monitoring the resonance of the micro-cantilever beam, wherein a change in the resonance determines the dew point.

16. The method of claim 15, wherein exciting the micro-cantilever beam into a vibratory mode comprises applying an electrical signal to a piezoelectric material which is coupled to the micro-cantilever beam, wherein the electrical signal causes the piezoelectric material to deform, thus causing the micro-cantilever beam to vibrate at a resonant frequency.

17. The method of claim 15, wherein decreasing the temperature of the micro-cantilever beam comprises the step of thermally coupling a cooling device to the micro-cantilever beam.

18. The method of claim 15, wherein decreasing the temperature of the micro-cantilever beam comprise the steps of:

forming a plurality of thermoelectric elements in thermal proximity to the micro-cantilever beam; and driving the thermoelectric elements to cool the micro-cantilever beam to a temperature at which the dew point is reached.

19. The method of claim 15, further comprising the step of identifying a temperature of the micro-cantilever beam at which the resonance changes.

20. The method of claim 19, wherein identifying the temperature comprises thermally coupling a temperature sensor to the micro-cantilever beam.

21. The method of claim 20, wherein the temperature sensor comprises one of a resistive temperature device, a thermocouple and a semiconductor device and thermally coupling the temperature sensor to the micro-cantilever beam comprises forming the temperature sensor on or near the micro-cantilever beam.

22. The method of claim 15, further comprising the step of increasing the temperature of the micro-cantilever beam to thereby cycle the temperature of the micro-cantilever beam for multiple dew point measurements.

* * * * *